(12) United States Patent
Kettle et al.

(10) Patent No.: US 6,613,760 B1
(45) Date of Patent: Sep. 2, 2003

(54) INDOLE DERIVATIVES AND THEIR USE AS MCP-1 RECEPTOR ANTAGONISTS

(75) Inventors: Jason Kettle, Macclesfield (GB); Alan W Faull, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/889,493

(22) PCT Filed: Jan. 31, 2000

(86) PCT No.: PCT/GB00/00271

§ 371 (c)(1),
(2), (4) Date: Jul. 2, 2001

(87) PCT Pub. No.: WO00/46197

PCT Pub. Date: Aug. 10, 2000

(30) Foreign Application Priority Data

Feb. 5, 1999 (GB) .............................................. 9902453

(51) Int. Cl.$^7$ ....................... A61K 31/33; A61K 31/404; C07D 417/00; C07D 413/00; C07D 209/42

(52) U.S. Cl. ..................... 514/183; 514/227.8; 514/378; 514/381; 514/419; 514/415; 514/359; 544/60; 544/62; 548/240; 548/250; 548/492

(58) Field of Search .............................. 514/183, 227.8, 514/378, 381, 419, 415, 359; 544/60, 62; 548/240, 250, 492

(56) References Cited

U.S. PATENT DOCUMENTS

| | | | |
|---|---|---|---|
| 3,557,142 A | 1/1971 | Bell ....................... | 260/326.13 |
| 3,776,923 A | 12/1973 | Remers et al. .......... | 260/326.13 |
| 3,997,557 A | 12/1976 | Helsley et al. .......... | 260/326.13 |
| 4,529,724 A | 7/1985 | Ho ............................... | 514/215 |
| 4,608,384 A | 8/1986 | Wierzbicki et al. .......... | 514/419 |
| 4,721,725 A | 1/1988 | Biller et al. ................... | 548/483 |
| 4,751,231 A | 6/1988 | Halczenko et al. .......... | 514/412 |
| 4,965,369 A | 10/1990 | Maetzel et al. .............. | 548/492 |
| 5,081,145 A | 1/1992 | Guindon et al. ............. | 514/419 |
| 5,190,968 A | 3/1993 | Gillard et al. ............... | 514/419 |
| 5,254,563 A | 10/1993 | Huth et al. ................... | 514/292 |
| 5,272,145 A | 12/1993 | Prasit et al. ............. | 514/227.8 |
| 5,273,980 A | 12/1993 | Frenette et al. ............. | 514/300 |
| 5,288,743 A | 2/1994 | Brooks et al. ............... | 514/365 |
| 5,290,798 A | 3/1994 | Gillard et al. ............... | 514/361 |
| 5,308,850 A | 5/1994 | Gillard et al. ............... | 514/301 |
| 5,389,650 A | 2/1995 | Frenette et al. ............. | 514/337 |
| 5,399,699 A | 3/1995 | Kolasa et al. ............... | 546/174 |
| 5,482,960 A | 1/1996 | Berryman et al. .......... | 514/414 |
| 5,684,032 A | 11/1997 | Elliot et al. ................. | 514/414 |
| 5,852,046 A | 12/1998 | Lang et al. .................. | 514/419 |
| 5,955,492 A | 9/1999 | Thompson et al. ......... | 514/419 |
| 6,184,235 B1 | 2/2001 | Connor et al. .............. | 514/322 |
| 6,337,344 B1 | 1/2002 | Defossa et al. | |

FOREIGN PATENT DOCUMENTS

| | | |
|---|---|---|
| DE | 298 913 a5 | 3/1992 |
| EP | 0 077 209 | 4/1983 |
| EP | 0 186 367 | 7/1986 |
| EP | 0 189 690 | 8/1986 |
| EP | 0 419 049 A1 | 3/1991 |
| EP | 0 480 659 A2 | 4/1992 |
| EP | 0 535 923 A1 | 4/1993 |
| EP | 0 535 924 A1 | 4/1993 |
| EP | 0 535 925 A1 | 4/1993 |
| EP | 0 535 926 A1 | 4/1993 |
| EP | 0 639 573 A1 | 2/1995 |
| EP | 0 822 185 | 2/1998 |
| EP | 0 275 667 | 7/1998 |
| FR | 2 565 981 | 12/1985 |
| JP | 63284177 | 11/1988 |
| JP | 4273857 | 9/1992 |
| WO | WO 86/00896 | 2/1986 |
| WO | WO 92/04343 | 3/1992 |
| WO | WO 93/12780 | 7/1993 |
| WO | WO 93/16069 | 8/1993 |
| WO | WO 93/20078 | 10/1993 |
| WO | WO 93/25546 | 12/1993 |
| WO | WO 94/14434 | 7/1994 |
| WO | WO 96/03377 | 2/1996 |
| WO | WO 96/31492 | 10/1996 |
| WO | WO 96/33171 | 10/1996 |
| WO | WO 96/37467 | 11/1996 |
| WO | WO 96/37469 | * 11/1996 |
| WO | 9637469 | * 11/1996 |
| WO | WO 97/12613 | 4/1997 |
| WO | WO 97/12615 | 4/1997 |
| WO | WO 97/30704 | 8/1997 |
| WO | WO 97/35572 | 10/1997 |
| WO | WO 98/06703 | 2/1998 |
| WO | WO 99/07351 | 2/1999 |
| WO | WO 99/07678 | 2/1999 |

OTHER PUBLICATIONS

Berman, J.W. et al. Localization of Monocyte Chemoattractant Peptide–1 Expression in the Central Nervous System in Experimental Autoimmune Encephalomyelitis and Trauma in the Rat. *J. Immunol.* 156, 3017–3023 (1996).

Bobosik, V. & Krutosikova, A. Synthesis of N–Phenylsufonyl Protected Furo[3,2–b]Pyrroles. *Collect, Czech. Chem. Commun.* 59, 499–502 (1994).

Dandarova, M. 13C NMR Spectra of Some Substituted Furo[3,2–b]pyrroles. *Magnetic Resonance Chem.* 28, 830–831 (1990).

Deleuran, M. et al. Localization of monocyte chemotactic and activating factor (MCAF/MCP–1) in psoriasis. *J. Dermatological Sci.* 13, 228–236 (1996).

(List continued on next page.)

Primary Examiner—Richard L. Daymond
Assistant Examiner—Sudhaker B. Patel
(74) Attorney, Agent, or Firm—Ropes & Gray LLP

(57) ABSTRACT

The present invention relates to certain novel compounds, including their production, their formulation as pharmaceutical compositions, and their therapeutic uses. In particular, the invention discloses certain indole derivatives and their function as inhibitors of monocyte chemoattractant protein-1 (MCP-1) and RANTES induced chemotaxis. The invention also discloses the use of the novel compounds in the treatment of inflammatory disease.

8 Claims, No Drawings

OTHER PUBLICATIONS

Grimm, M.C. et al. Enhanced expression and production of monocyte chemoattractant protein–1 in inflammatory bowel disease mucosa. *J. Leukocyte Biol.* 59, 804–812 (Jun. 1996).

Harrison, C.–A. et al. Cyclopenta [b] indoles. Part 2. Model studies towards the tremorgenic mycotoxins. *J. Chem. Soc. Perkin Trans.* 1131–1136 (1995).

Hartman, G.D. & Halczenko, W. The Synthesis of 5–Alkylaminomethylthieno[2,3–b]pyrrole–5–sulfonamides. *Heterocycles* 29, 1943–1949 (1989).

Jones, M.L. et al. Potential Role of Monocyte Chemoattractant Protein 1/JE in Monocyte/Macrophage–Dependent IgA Immune Complex Alveolitis in the Rat. *J. Immunol.* 149, 2147–2154 (Sep. 15, 1992).

Kataoka, K. et al., Homopiperazines as cell migration inhibitors. *Chemical Abstracts*, Columbus Ohio, US 123, 667 (Oct. 2, 1995).

Koch, A.E. et al. Enhanced Production of Monocyte Chemoattractant Protein–1 Rheumatoid Arthritis. *J. Clin. Invest.* 90, 772–779 (Sep. 1992).

Korobchenko, L.V. et al. Synthesis and antiviral activity of pyrrolecarboxylic acids and their derivatives. *Chemical Abstracts* Columbus, Ohio, Access No.: 119:62465 (1995).

Krutosikova, A. & Dandarova, M. Substituted Vinyl Azides in Synthesis of Furo[3,2–b:4,5–b]–Dipyrroles and Pyrrolo[2',3':4,5]Furo[3,2–c]Pyridines. *Heterocycles* 37, 1695–1700 (1994).

Krutosikova, A. & Dandarova, M. Reactions of Methyl 2–Formylfuro[3,2–b]pyrrole–5–carboxylates. *Chem. Papers* 50, 72–76 (1996).

Krutosikova, A. & Hanes, M. Substituted 4–Benzylfuro[3,2–b]Pyrroles. *Collect Czech Chem.* 57, 1487–1494 (1992).

Krutosikova, A. et al., Condensed O–, N–Heterocycles by the Transformation of Azidoacrylates. *Chemical Monthly* 123, 807–815 (1992).

Krutosikova, A. et al. Derivatives of Furo[3,2–b]Pyrrole. *Collect. Czech. Chem. Commun.* 59, 473–481 (1994).

Krutosikova, A. et al. Substituted Vinyl Azides in the Synthesis of Condensed Nitrogen Heterocycles. *Chem. Papers* 48, 268–273 (1994).

Krutosikova, A. et al. Synthesis and Reactions of Furo[3,2–b]Pyrrole Type Aldehydes. *Collect. Czech. Chem Commune.* 58, 2139–2149 (1993).

Murakami, Y. et al., Direct Regioselective Vinylation of Indoles Using Palladium (II) Chloride. *Heterocycles* 22, 1493–1496 (1984).

Rosenmund, P. et al. Decarboxylations of Some 1–Alkyl–2–carboxy–3–indolacetic Acids and Synthesis of a 5–Thiocyanato–2,3–dihydroindole. *Chem. Ber.* 108, 3538–3542 (1975).—Abstract only.

Troschutz, R. & Hoffmann, A. Synthesis of Substituted 3–Amino–4–cyano–1–oxo–1,2,5,10–tetrahy–droazepino[3,4–b]indoles. *J. Heterocyclic Chem.* 34, 1431 (1997).

Yokoyama, Y. et al., New Synthetic Method for Dehydrotryptophan Derivatives. Synthesis Studies on Indoles and Related Compounds. XXIV. *Chem. Pharm. Bull.* 42, 832–838 (1994).

Krutosikova, A. et al. Synthesis and Reactions of Furo[2,3–b]pyrroles. Molecules 2, 69–79 (1997).

Yokoyama, Y. et al. Palladium–Catalyzed Cross–Coupling Reaction: Direct Allylation of Aryl Bromides with Allyl Acetate. *Tetrahedron Letters* 26, 6457–6460 (1985).

\* cited by examiner

INDOLE DERIVATIVES AND THEIR USE AS MCP-1 RECEPTOR ANTAGONISTS

This application is the National Phase of International Application PCT/GB00/00271 filed Jan. 31, 2000 which designated the U.S. and that International Application was published under PCT Article 21(2) in English.

The present invention relates to chemical compounds, to their production as well as to pharmaceutical compositions containing them as well as to their use in therapy, in particular of inflammatory disease.

MCP-1 is a member of the chemokine family of pro-inflammatory cytokines which mediate leukocyte chemotaxis and activation. MCP-1 is a C—C chemokine which is one of the most potent and selective T-cell and monocyte chemoattractant and activating agents known. MCP-1 has been implicated in the pathophysiology of a large number of inflammatory diseases including rheumatoid arthritis, glomerular nephritides, lung fibrosis, restenosis (International Patent Application WO 94/09128), alveolitis (Jones et al., 1992, *J. Immunol.*, 149, 2147) and asthma. Other disease areas where MCP-1 is thought to play a part in their pathology are atherosclerosis (e.g. Koch et al., 1992, *J. Clin. Invest.*, 90, 772–779), psoriasis (Deleuran et al., 1996, *J. Dermatological Science*, 13, 228–236), delayed-type hypersensitivity reactions of the skin, inflammatory bowel disease (Grimm et al., 1996, *J. Leukocyte Biol.*, 59, 804–812), multiple sclerosis and brain trauma (Berman et al. 1996, *J. Immunol.*, 156, 3017–3023). An MCP-1 inhibitor may also be useful to treat stroke, reperfusion injury, ischemia, myocardial infarction and transplant rejection.

MCP-1 acts through the MCP-1 receptor (also known as the CCR2 receptor). MCP-2 and MCP-3 may also act, at least in part, through the MCP-1 receptor. Therefore in this specification, when reference is made to "inhibition or antagonism of MCP-1" or "MCP-1 mediated effects" this includes inhibition or antagonism of MCP-2 and/or MCP-3 mediated effects when MCP-2 and/or MCP-3 are acting through the MCP-1 receptor.

Copending International Patent Application Nos. PCT/GB98/02340 and PCT/GB98/02341 describe and claim groups of compounds based upon the indole ring structure which are inhibitors of MCP-1 and therefore have applications in therapy.

The use of certain indole derivatives as NMDA antagonists is described is U.S. Pat. No. 5,051,442, WO9312780, EP-483881. Other indoles and their use as inhibitors of leukotriene biosynthesis is described in for example, EP-A-275-667.

The applicants have found a particular substitution on the indole ring produces advantageous results when used therapeutically as inhibitors of MCP-1.

According to the present invention there is provided a compound of formula (I)

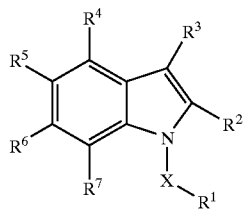

(I)

X is $CH_2$ or $SO_2$
$R^1$ is an optionally substituted aryl or heteroaryl ring;

$R^2$ is carboxy, cyano, —$C(O)CH_2OH$, —$CONHR^8$, —$SO_2NHR^8$, tetrazol-5-yl, $SO_3H$, or a group of formula (VI)

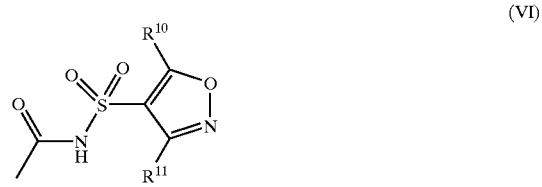

(VI)

where $R^8$ is selected from hydrogen, alkyl, aryl, cyano, hydroxy, —$SO_2R^{12}$ where $R^{12}$ is alkyl, aryl, heteroaryl, or haloalkyl, or $R^8$ is a group-$(CHR^{13})_r$—COOH where r is an integer of 1–3 and each $R^{13}$ group is independently selected from hydrogen or alkyl; $R^9$ is hydrogen, alkyl, optionally substituted aryl such as optionally substituted phenyl or optionally subtituted heteroaryl such as 5 or 6 membered heteroaryl groups, or a group $COR^{14}$ where $R^{14}$ is alkyl, aryl, heteroaryl or haloalkyl; $R^{10}$ and $R^{11}$ are independently selected from hydrogen or alkyl, particularly $C_{1-4}$ alkyl;

$R^3$ is hydrogen, a functional group, optionally substituted alkyl, optionally substituted alkenyl, optionally substituted alkynyl, optionally substituted aryl, optionally substituted heterocyclyl, optionally substituted alkoxy, optionally substituted aralkyl, optionally substituted aralkyloxy, optionally substituted cycloalkyl;

$R^4$ is a group $C(O)NR^{15}R^{16}$ or a group $(CH_2)_t R^{17}$;
where $R^{15}$ and $R^{16}$ are independently selected from hydrogen, optionally substituted alkyl, optionally substituted alkenyl, optionally substituted alkynyl, optionally substituted cycloalkyl or optionally substituted heterocyclyl provided that $R^{15}$ and $R^{16}$ are not both hydrogen, or $R^{15}$ and $R^{16}$ together with the nitrogen atom to which they are attached form an optionally substituted heterocyclic ring which optionally contains further heteroatoms;
$R^{17}$ is selected from $NR^{18}R^{19}$, $OR^{20}$ or $S(O)_s R^{21}$
where $R^{18}$ and $R^{19}$ are independently selected from hydrogen, optionally substituted hydrocarbyl or optionally substituted heterocyclyl, or $R^{18}$ and $R^{19}$ together with the nitrogen atom to which they are attached form an optionally substituted heterocyclic ring which optionally contains further heteroatoms;
$R^{20}$ is substituted alkyl, optionally substituted alkenyl, optionally substituted alkynyl, optionally substituted cycloalkyl or optionally substituted heterocyclyl,
$R^{21}$ is optionally substituted hydrocarbyl or optionally substituted heterocyclyl, s is 0, 1 or 2 and t is an integer of from 1–4;

$R^5$, $R^6$ and $R^7$ are independently selected from hydrogen, a functional group or an optionally substituted hydrocarbyl groups or optionally substituted heterocyclyl groups.

In addition, the invention provides a pharmaceutically acceptable salt, in vivo hydrolysable ester, or amide of the compound of formula (I).

Compounds of formula (I) are inhibitors of monocyte chemoattractant protein-1. In addition, they appear to inhibit RANTES induced chemotaxis. RANTES is another chemokine from the same family as MCP-1, with a similar biological profile, but acting though the CCR1 receptor. As a result, these compounds can be used to treat disease mediated by these agents, in particular inflammatory disease. Thus the invention further provides a compound of formula (I) for use in the treatment of inflammatory disease.

In this specification the term 'alkyl' when used either alone or as a suffix includes straight chained, branched structures. These groups may contain up to 10, preferably up to 6 and more preferably up to 4 carbon atoms. Similarly the terms "alkenyl" and "alkynyl" refer to unsaturated straight or branched structures containing for example from 2 to 10, preferably from 2 to 6 carbon atoms. Cyclic moieties such as cycloalkyl, cycloalkenyl and cycloalkynyl are similar in nature but have at least 3 carbon atoms. Terms such as "alkoxy" comprise alkyl groups as is understood in the art.

The term "halo" includes fluoro, chloro, bromo and iodo. References to aryl groups include aromatic carbocylic groups such as phenyl and naphthyl. The term "heterocyclyl" or "heterocyclic" includes aromatic or non-aromatic rings, for example containing from 4 to 20, suitably from 5 to 8 ring atoms, at least one of which is a heteroatom such as oxygen, sulphur or nitrogen. Nitrogen heteroatoms may be substituted for example with hydrogen or hydrocarbyl depending on the available bonds. Sulphur atoms may be in the form of S, S(O) or S(O)$_2$.

Examples of such groups include furyl, thienyl, pyrrolyl, pyrrolidinyl, imidazolyl, triazolyl, thiazolyl, tetrazolyl, oxazolyl, isoxazolyl, pyrazolyl, pyridyl, pyrimidinyl, pyrazinyl, pyridazinyl, triazinyl, quinolinyl, isoquinolinyl, quinoxalinyl, benzothiazolyl, benzoxazolyl, benzothienyl or benzofuryl.

"Heteroaryl" refers to those groups described above which have an aromatic character. The term "aralkyl" refers to aryl substituted alkyl groups such as benzyl.

Other expressions used in the specification include "hydrocarbyl" which refers to any structure comprising carbon and hydrogen atoms. For example, these may be alkyl, alkenyl, alkynyl, aryl, heterocyclyl, alkoxy, aralkyl, cycloalkyl, cycloalkenyl or cycloalkynyl.

The term "functional group" refers to reactive substituents. They may comprise electron-donating or electron-withdrawing. Examples of such groups include halo, cyano, nitro, C(O)$_n$R$^{22}$, OR$^{22}$, S(O)$_m$R$^{22}$, NR$^{23}$R$^{24}$, C(O)NR$^{23}$R$^{24}$, OC(O)NR$^{23}$R$^{24}$, —NR$^{23}$C(O)$_n$R$^{22}$, —NR$^{22}$CONR$^{23}$R$^{24}$, —N=CR$^{22}$R$^{23}$, S(O)$_m$NR$^{23}$R$^{24}$ or —NR$^{23}$S(O)$_m$R$^{22}$ where R$^{22}$, R$^{23}$ and R$^{24}$ are independently selected from hydrogen or optionally substituted hydrocarbyl, or R$^{23}$ and R$^{24}$ together form an optionally substituted heterocyclic ring as defined above, which optionally contains further heteroatoms such as sulphur, S(O), SO$_2$, oxygen and nitrogen, n is an integer of 1 or 2, m is an integer of 1–2.

Suitable optional substituents for hydrocarbyl or groups R$^{22}$, R$^{23}$ and R$^{24}$ include halo, perhaloalkyl such as trifluoromethyl, mercapto, hydroxy, carboxy, alkoxy, heteroaryl, heteroaryloxy, alkenyloxy, alkynyloxy, alkoxyalkoxy, aryloxy (where the aryl group may be substituted by halo, nitro, or hydroxy), cyano, nitro, amino, mono- or di-alkyl amino, oximino or S(O)$_{m'}$R$^{25}$ where m' is 1 or 2 and R$^{25}$ is alkyl.

Where R$^{23}$ and R$^{24}$ form a heterocyclic group, this may be optionally substituted by hydrocarbyl such as alkyl as well as those substituents listed above for hydrocarbyl groups.

Suitable substituents for hydrocarbyl or heterocyclic groups R$^5$, R$^6$ and R$^7$ include those listed above for R$^{22}$, R$^{23}$ and R$^{24}$.

Suitably R$^1$ is an optionally substituted phenyl, pyridyl, naphthyl, furyl or thienyl ring, and in particular is a substituted phenyl or pyridyl ring.

Suitable optional substituents for R$^1$ in formula (I) include alkyl, alkenyl, alkynyl, halo, haloalkyl including perhaloalkyl such as trifluoromethyl, mercapto, alkoxy, haloalkoxy, alkenyloxy, alkynyloxy, hydroxyalkoxy, alkoxyalkoxy, alkanoyl, alkanoyloxy, cyano, nitro, amino, mono- or di-alkyl amino, oximino, sulphonamido, carbamoyl, mono or dialkylcarbamoyl or S(O)$_m$R$^{26}$ where m is as defined above and R$^{26}$ is hydrocarbyl.

Particular examples of substituents R$^5$, R$^6$ and R$^7$ include hydrogen, hydroxy, halo, optionally substituted alkyl such as aralkyl, carboxyalkyl or the amide derivative thereof; alkoxy; aryloxy; aralkyloxy; or an amino group which is optionally substituted with alkyl, aryl or aralkyl. A specific functional group which is suitable for R$^5$, R$^6$ and/or R$^7$ is a group of sub-formula (IV).

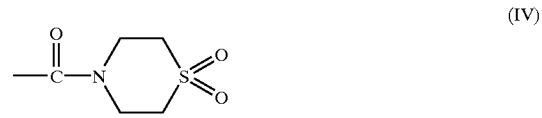

(IV)

Particular examples of groups R$^5$, R$^6$ and R$^7$ are hydrogen, hydroxy, halo or alkoxy. In particular R$^6$ and R$^7$ are hydrogen. R$^5$ may be hydrogen but in addition is suitably a small subsituent such as hydroxy, halo or methoxy.

Particular substituents for R$^1$ include trifluoromethyl, C$_{1-4}$alkyl, halo, trifluoromethoxy, C$_{1-4}$alkoxy, C$_{1-4}$alkanoyl, C$_{1-4}$alkanoyloxy, nitro, carbamoyl, C$_{1-4}$alkoxycarbonyl, C$_{1-4}$alkylsulphanyl, C$_{1-4}$alkylsulphinyl, C$_{1-4}$alkylsulphonyl, sulphonamido, carbamoylC$_{1-4}$alkyl, N—(C$_{1-4}$alkyl)carbamoylC$_{1-4}$alkyl, N—(C$_{1-4}$alkyl)$_2$carbamoyl-C$_{1-4}$alkyl, hydroxyC$_{1-4}$alkyl or C$_{1-4}$alkoxyC$_{1-4}$alkyl.

Additionally or alternatively, two such substituents together may form a divalent radical of the formula —O(CH$_2$)$_{1-4}$O— attached to adjacent carbon atoms on the R$^1$ ring.

Preferred substituents for R$^1$ are one or more non-polar substituents such as halo.

In particular, R$^1$ is substituted by one or more halo groups, in particular chlorine. A particular example of an R$^1$ group is 3,4-dichlorophenyl, 3-fluoro-4-chlorophenyl, 3-chloro-4-fluorophenyl or 2,3-dichloropyrid-5-yl.

Examples of groups R$^2$ include carboxy; cyano; tetrazol-5-yl; SO$_3$H; —CONHR$^8$ where R$^8$ is selected from cyano, hydroxy, —SO$_2$R$^{12}$ where R$^{12}$ is alkyl such as C$_{1-4}$ alkyl, aryl such as phenyl, heteroaryl or trifluoromethyl, or R$^8$ is a group-(CHR$^{10}$)$_r$—COOH where r is an integer of 1–3 and each R$^{10}$ group is independently selected from hydrogen or alkyl such as C$_{1-4}$ alkyl; or R$^2$ is a group —SO$_2$NHR$^9$ where R$^9$ is an optionally substituted phenyl or an optionally substituted 5 or 6 membered heteroaryl group, or a group COR$^{14}$ where R$^{14}$ is alkyl such as C$_{1-4}$ alkyl, aryl such as phenyl, heteroaryl or trifluoromethyl, or R$^2$ is a group of formula (VI)

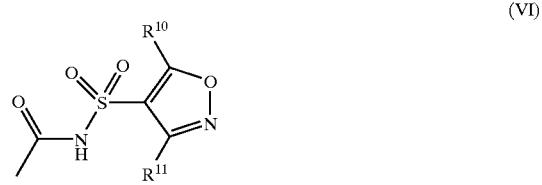

(VI)

where R$^{10}$ and R$^{11}$ are independently selected from hydrogen or alkyl, particularly C$_{1-4}$ alkyl.

Preferably $R^2$ is carboxy or a pharmaceutically acceptable salt or ester thereof.

Suitable groups $R^3$ include hydrogen, fluoro, chloro, bromo, iodo, methyl, cyano, trifluoromethyl, hydroxymethyl, alkoxyalkyl such as $C_{1-4}$alkoxymethyl, methoxy, benzyloxy, carboxyalkoxy such as carboxymethoxy, methylsulphanyl, methylsulphinyl, methylsulphonyl or carboxy$C_{3-6}$cycloalkyl, —(CHR$^{27}$)$_r$—NR$^{28}$R$^{29}$ (where r is 0–2, each $R^{27}$ is independently hydrogen or alkyl, in particular $C_{1-4}$ alkyl, $R^{28}$ and $R^{29}$ are independently selected from H and $C_{1-4}$alkyl or $R^{28}$ and $R^{29}$ together with the nitrogen to which they are attached form a 5 or 6 membered ring optionally containing one further heteroatom selected from O, N, S, S(O) or SO$_2$. Suitably $R^{28}$ and $R^{29}$ together form a heterocylic ring such as morpholino or piperazinyl.

Other such groups $R^3$ include optionally substituted aryl groups, such as optionally substituted phenyl or naphthyl group. Suitable substituents for phenyl groups $R^3$ include one or more groups selected from chlorine, fluorine, methyl, trifluoromethyl, trifluoromethoxy, amino, formyl, phenyl, methoxy, phenoxy or phenyl.

$R^3$ may comprise a range of substituents as listed above, in particular, hydrogen or a small substituent group such as $C_{1-4}$alkyl in particular methyl, or trifluoromethyl, and is preferably hydrogen.

Suitable substitutents for hydrocarbyl and heterocyclic groups $R^{15}$, $R^{16}$, $R^{18}$, $R^{19}$, $R^{20}$ and $R^{21}$ as they appear in the definition of $R^4$ include those listed above in relation to $R^{22}$, $R^{23}$ and $R^{24}$.

Examples of $R^4$ are groups C(O)NR$^{15}$R$^{16}$ where one of $R^{15}$ or $R^{16}$ is hydrogen or alkyl such as methyl, and the other is optionally substituted heterocyclyl or optionally substituted alkyl such as $C_{1-2}$ alkyl in particular methyl, or $R^{15}$ and $R^{16}$ together with the nitrogen atom to which they are attached form an optionally substituted heterocyclic ring which optionally contains further heteroatoms. Suitable optional substitutents for heterocyclic groups $R^{15}$ or $R^{16}$ in this case are alkyl groups such as methyl, or oxo groups. Suitable optional substitutents for alkyl groups $R^{15}$ and $R^{16}$ include one or more groups selected from amino; mono- or di-alkyl amino; carboxy; heterocyclyl optionally substituted with for example an alkyl groups such as methyl or an oxo group; or a group NHSO$_2$R$^{30}$ where $R^{30}$ is alkyl such as methyl.

A preferred group for $R^4$ is a group C(O)NR$^{15}$R$^{16}$ where one of $R^{15}$ or $R^{16}$ is hydrogen and the other is heterocyclyl or alkyl substituted with one or more groups selected from amino, mono- or di-alkyl amino, carboxy or optionally substituted heterocyclyl, or $R^{15}$ and $R^{16}$ together with the nitrogen atom to which they are attached form an optionally substituted heterocyclic ring which optionally contains further heteroatoms.

Where one of $R^{15}$ or $R^{16}$ is hydrogen, examples of suitable heterocyclyls for the other include imidazole, imidazolinone, or tetrahydrothiophene-1,1-dioxide.

Preferably one of $R^{15}$ or $R^{16}$ is hydrogen and the other is optionally substituted alkyl, for example $C_{1-2}$ alkyl. Suitable substituents include one or more groups selected from amino, mono- or di-alkyl amino, a group NHSO$_2$R$^{30}$ where $R^{30}$ is methyl, carboxy or optionally substituted heterocyclyl, such as isoxazole optionally substituted mono or di-substituted with alkyl, such as methyl.

Where $R^{15}$ and $R^{16}$ together with the nitrogen atom to which they are attached form an optionally substituted heterocyclic ring which optionally contains further heteroatoms, that ring is, for example a morpholine ring. Alternatively, $R^4$ is a group of sub-formula (IV) as listed above.

Alternatively, $R^4$ is preferably a group (CH$_2$)$_t$ $R^{17}$ where t is 1 and $R^{17}$ is a group NR$^{18}$R$^{19}$. Particular examples of $R^{18}$ and $R^{19}$ include hydrogen and optionally substituted alkyl, or $R^{18}$ and $R^{19}$ together with the nitrogen atom to which they are attached form an optionally substituted heterocyclic ring which optionally contains further heteroatoms, such as pyrazole or tetrahydropyranyl. In particular, $R^{18}$ and $R^{19}$ together form a morpholine ring.

X is CH$_2$ or SO$_2$ and is preferably CH$_2$.

Suitable pharmaceutically acceptable salts of compounds of formula (I) include acid addition salts such as methanesulfonate, fumarate, hydrochloride, hydrobromide, citrate, maleate and salts formed with phosphoric and sulphuric acid. In another aspect suitable salts are base salts such as an alkali metal salt for example sodium, an alkaline earth metal salt for example calcium or magnesium, an organic amine salt for example triethylamine, morpholine, N-methylpiperidine, N-ethylpiperidine, procaine, dibenzylamine, N,N-dibenzylethylamine or amino acids for example lysine. There may be more than one cation or anion depending on the number of charged functions and the valency of the cations or anions. A preferred pharmaceutically acceptable salt is a sodium salt.

An in vivo hydrolysable ester of a compound of the formula (I) containing carboxy or hydroxy group is, for example, a pharmaceutically acceptable ester which is hydrolysed in the human or animal body to produce the parent acid or alcohol.

Suitable pharmaceutically acceptable esters for carboxy include alkyl esters, such as $C_{1-6}$ alkyl esters for example, ethyl esters, $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl and may be formed at any carboxy group in the compounds of this invention.

Suitable pharmaceutically acceptable esters of compounds of formula (I) are in vivo hydrolysable ester of a compound of the formula (I) containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxymethoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl.

Esters which are not in vivo hydrolysable are useful as intermediates in the production of the compounds of formula (I) and therefore these form a further aspect of the invention.

Thus examples of compounds of formula (I) include the following:

TABLE 1
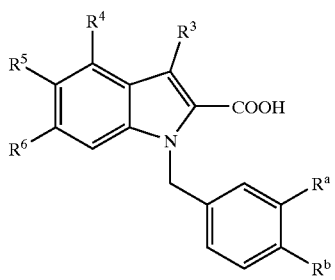
| Compd No. | R³ | R⁴ | R⁵ | R⁶ | Rᵃ | Rᵇ |
|---|---|---|---|---|---|---|
| 1 | H |  | H | H | Cl | Cl |
| 2 | H | 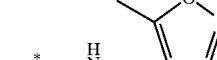 | H | H | Cl | Cl |
| 3 | H |  | H | H | Cl | Cl |
| 4 | H | 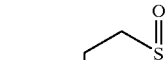 | H | H | Cl | Cl |
| 5 | H | $CH_2N(CH_3)_2$ | OH | H | Cl | Cl |
| 6 | H | $C(O)NH(CH_2)_2N(CH_3)_2$ | H | H | Cl | Cl |
| 7 | H | 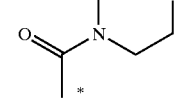 | H | H | Cl | Cl |
| 8 | H |  | H | H | Cl | Cl |
| 9 | H | $C(O)NH(CH_2)_2NHS(O)_2CH_3$ | H | H | Cl | Cl |
| 10 | H | 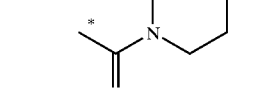 | H | H | Cl | Cl |

TABLE 1-continued

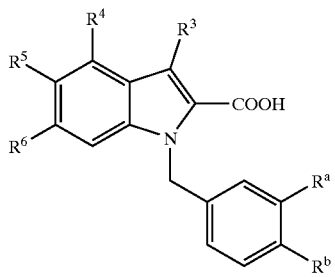

| Compd No. | R³ | R⁴ | R⁵ | R⁶ | Rᵃ | Rᵇ |
|---|---|---|---|---|---|---|
| 11 | H |  | H | H | Cl | Cl | where * indicates the point of attachment of the group to the indole ring.

Yet a further aspect of the invention provides pharmaceutical compositions comprising a compound of formula (I) as defined above.

Compounds of formula (I) are suitably prepared by methods such as those described in International Patent Application Nos. PCT/GB98/02340 and PCT/GB98/02341.

In particular compounds of formula (I) can be prepared by reacting a compound of formula (VII)

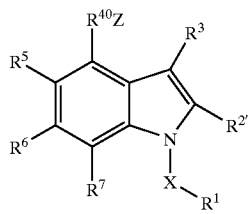

(VII)

where $X$, $R^1$, $R^3$, $R^5$, $R^6$ and $R^7$ are as defined in relation to formula (I) and $R^{2'}$ is a group $R^2$ as defined in relation to formula (I) or a protected form thereof, $R^{40}$ is a group $C(O)$ or a group $(CH_2)_t$ where t is as defined in relation to formula (I) and Z is a leaving group, either (a) when $R^{40}$ is $C(O)$, with a compound of formula (VIII)

 (VIII)

where $R^{15}$ and $R^{16}$ are as defined in relation to formula (I);

or (b) where $R^{40}$ is group $(CH_2)_t$ with a compound of formula (IX)

 (IX)

where $R^{17}$ is as defined in relation to formula (I);
and thereafter if necessary or desirable, deprotecting a group $R^{2'}$ to a group $R^2$ or changing a group $R^2$ to a different such group.

Suitable leaving groups for Z include halo such as chloro. The reaction is suitably effected in an organic solvent such as dichloromethane or tetrahydrofuran in the presence of a base such as triethylamine. Moderate temperatures, for example of from 0° to 50° C. and conveniently ambient temperature may be employed.

The compounds of formula (VII) suitably have an ester group as $R^{2'}$. Such compounds can then be converted to the corresponding acid by desterification, for example using sodium hydroxide in a mixture of methanol and tetrahydrofuran.

Compounds of formula (VII) where $R^{40}$ is $C(O)$ are suitably prepared in situ by reaction of the corresponding carboxylic acid with a halogenating agent such as oxalyl chloride. The acid is suitably derived from a compound of formula (X)

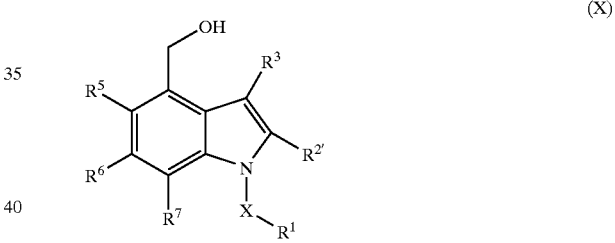 (X)

where $X$, $R^1$, $R^{2'}$, $R^3$, $R^5$, $R^6$ and $R^7$ are as defined above, by a sequence of reactions in which the hydroxy methyl group is first converted to a carboxaldehyde for example by reaction with 2,3-dichloro-5,6-dicyanobenzoquinone, which is then oxidised to the corresponding acid using conventional methods.

Compounds of formula (X) are suitably prepared by reacting a compound of formula (XI)

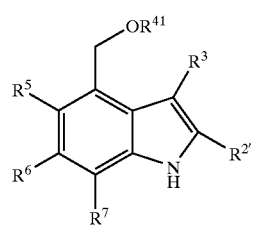 (XI)

where $X$, $R^{2'}$, $R^3$, $R^5$, $R^6$ and $R^7$ are as defined above and $R^{41}$ is a protecting group, with a compound of formula (XII)

 (XII)

where $R^1$ and $X$ are as defined in relation to formula (I) and $Z^1$ is a leaving group; and thereafter removing the protecting group $R^{41}$.

Suitable leaving groups for $Z^1$ include halide such as chloride, bromide or iodide, as well as mesylate or tosylate. The reaction is suitably effected in an organic solvent such as dimethylformamide (DMF) tetrahydrofuran (THF) or DCM in the presence of a base such as sodium hydride, sodium hydroxide, potassium carbonate. Optionally the reaction is effected in the presence of a suitable phase transfer catalyst. The choice of base and solvent is interdependent to a certain extent in that certain solvents are compatible with some bases only as is understood in the art. For example, sodium hydride may preferably be used with dimethylformamide or tetrahydrofuran and sodium hydroxide is preferably used with dichloromethane and a phase transfer catalyst.

The reaction can be carried out at moderate temperatures, for example from 0 to 50° C. and conveniently at about ambient temperature.

Preferably, $R^{2'}$ is an ester group in the compound of formula IX and this may be subsequently converted to an acid or to another ester or salt, by conventional methods later in the process.

Suitable protecting groups $R^{41}$ include acetyl, benzyl or tetrahydrpyranyl. The reaction conditions employed will be variable depending upon the nature of the protecting group $R^{40}$ and would be apparent to a skilled person. Acetyl groups may be removed by reaction with a strong base such as sodium methoxide, whereas benzyl groups may be removed by hydrogenation, for example in the presence of a catalyst such as palladium catalyst. Removal of tetrahydropyranyl protecting groups may be effected using p-toluenesulphonic acid as illustrated hereinafter.

Compounds of formula (X) may be prepared by cyclisation of a compound of formula (XIII)

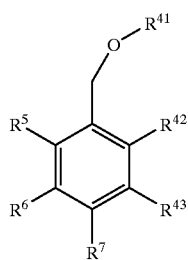

(XIII)

where $R^5$, $R^6$, $R^7$ and $R^{41}$ are as defined above and $R^{42}$ and $R^{43}$ represent a combination of moieties which can cyclise to form an appropriately substituted pyrrole ring. For example, $R^{42}$ can be a group of formula —CH=C($R^{44}$)N$_3$ where $R^{44}$ is a group $R^2$ as defined above, or a protected form thereof, and $R^{43}$ may be hydrogen. Cyclisation to form a compound of formula (XII) may then be effected by heating for example under reflux in an organic solvent, in particular a high boiling aprotic solvent such as xylene or toluene.

Alternatively, $R^{43}$ may be nitro and $R^{42}$ may be a group of formula —CH$_2$C(O)$R^{2'}$ where $R^{2'}$ is as defined above in relation to formula (VII). These compounds will cyclise in the presence of a catalyst such as palladium on carbon in the presence of hydrogen. The reaction may be effected at moderate temperatures for example of from 0 to 80° C., conveniently at about ambient temperature.

Thus examples of compounds of formula (XIII) include compounds of formula (XIV) and (XV)

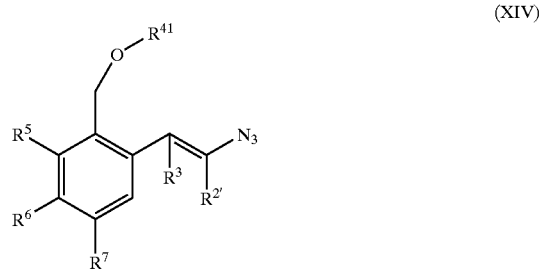

(XIV)

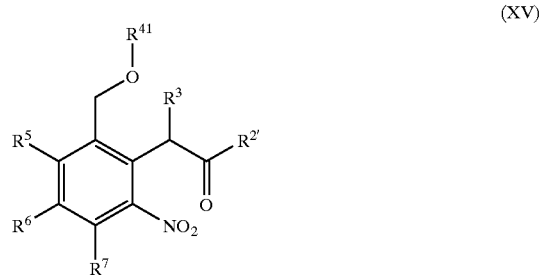

(XV)

Compounds of formula (XIII) where $R^3$ is hydrogen may be prepared for example by reacting a compound of formula (XVI)

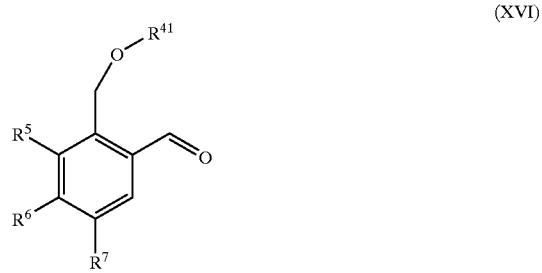

(XVI)

with a compound of formula (XVII)

N$_3$CH$_2$R$^{2'}$ (XVII)

where $R^5$, $R^6$, $R^7$, $R^{41}$, and $R^{2'}$ are as defined hereinbefore. The reaction may be effected in an organic solvent such as ethanol at low temperatures of from −20 to 0° C., suitably at about 0° C. The reaction is suitably effected in the presence of a base such as an alkoxide, in particular an ethoxide, for example potassium ethoxide.

Where necessary or desired, $R^3$ can be converted from hydrogen to a different group $R^3$ subsequently in the reaction scheme, using conventional methods.

Compounds of formula (XVII) are suitably prepared by reacting a compound of formula (XVIII)

R$^{47}$CH$_2$R$^{2'}$ (XVIII)

where $R^{2'}$ is as defined above and $R^{47}$ is a leaving group such as halide and in particular bromide, with an azide salt, such as an alkali metal azide salt in particular sodium azide.

Compounds of formula (XV) may be prepared by reacting a compound of formula (XIX)

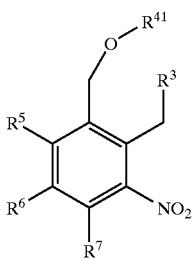

(XIX)

where $R^5$, $R^6$, $R^7$, $R^3$, $R^{40}$ and $R^{2'}$ are as defined above, with a compound of formula (XX)

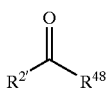

(XX)

where $R^{2'}$ is as defined above and $R^{48}$ leaving group such as hydroxy. Examples of compounds of formula (XX) are oxalates such as diethyloxalate. The reaction is suitably effected in the presence of a base such as sodium hydride in an organic solvent such as THF. Moderate temperatures of from 0° to 40° C. and conveniently ambient temperature is employed.

Compounds of formula (VII) where $R^{40}$ is $(CH_2)_t$ may be prepared by halogenation of a compound of formula (XXI)

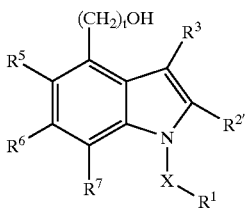

(XXI)

where t, $R^1$, $R^{2'}$, $R^3$, $R^5$, $R^6$ and $R^7$ are as defined above Compound (X) above is a particular example of a compound of formula (XXI) and others may be prepared by analogous methods to those described for formula (X).

Compounds of formula (XI), (XVI), (XVII), (XVIII), (XIX) and (XX) are either known compounds or they can be prepared from known compounds by conventional methods.

According to a further aspect of the invention there is provided a compound of the formula (I) as defined herein, or a pharmaceutically acceptable salt or an in vivo hydrolysable ester thereof, for use in a method of treatment of the human or animal body by therapy. In particular, the compounds are used in methods of treatment of inflammatory disease.

According to a further aspect of the present invention there is provided a method for antagonising an MCP-1 mediated effect in a warm blooded animal, such as man, in need of such treatment, which comprises administering to said animal an effective amount of a compound of formula (I), or a pharmaceutically acceptable salt, or an in vivo hydrolysable ester thereof.

The invention also provides a compound of formula (I) as defined herein, or a pharmaceutically acceptable salt, or an in vivo hydrolysable ester thereof, for use as a medicament.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal track, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxyethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient faith a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedure well known in the art.

Compositions for administration by insufflation may be in the form of a finely divided powder containing particles of average diameter of, for example, 30µ or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on Formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain. for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board). Pergamon Press 1990.

The size of the dose for therapeutic or prophylactic purposes of a compound of the Formula I will naturally vary according to the nature and severity of the conditions, the age and sex of the animal or patient and the route of administration, according to well known principles of medicine. As mentioned above, compounds of the Formula I are useful in treating diseases or medical conditions which are due alone or in part to the effects of farnesylation of rats.

In using a compound of the Formula I for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per keg body weight will generally be used. Similarly, for administration by inhalation, a dose in the range, for example, 0.5 mg to 25 mg per kg body weight will be used. Oral administration is however preferred.

The invention is further illustrated, but not limited by the following Examples in which the following general procedures were used unless stated otherwise.

Preparation 1
Ethyl N-(3,4-dichlorobenzyl)-4-(2-tetrahydropyranyloxy) methylindole-2-carboxylate Ethyl-4-(2-tetrahydropyranyloxy)methylindole-2-carboxylate (5.1 g) (Chung-gi Shen et al., Heterocycles, 43, 1996, 891–898) and sodium hydride (741 mg, 60% in mineral oil) were stirred in DMF (100 ml) under argon at ambient temperature for 0 minutes. 3,4-Dichlorobenzyl chloride (2.79 ml) was added and the mixture stirred overnight, then partitioned between ethyl acetate (150 ml) and water (150 ml). The organic phase was washed with water (2×150 ml), dried (MgSO$_4$), concentrated in vacuo and the residue purified by column chromatography using iso-hexane, then ethyl acetate:iso-hexane (5/95) as eluent to give the product as a yellow oil (4.39 g, 56%); NMR δ(CDCl$_3$) 1.40 (t, 3H), 1.50–2.00 (m, 6H), 3.60 (m, 1H), 4.00 (m, 1H), 4.35 (q, 2H), 4.75 (m, 1H), 4.85 (d, 1H), 5.10 (d, 1H), 5.80 (s, 2H), 6.85 (m, 1H), 7.15–7.40 (m, 5H), 7.50 (s, 1H); M/z (+) 462.5 (MH$^+$).

Preparation 2
Ethyl N-(3,4-dichlorobenzyl)-4-hydroxymethylindole-2-carboxylate

Ethyl N-(3,4-dichlorobenzyl)-4-(2-tetrahydropyranyloxy) methylindole-2-carboxylate (4.38 g) and p-toluenesulphonic acid (100 mg) in ethanol (100 ml) was stirred at ambient temperature for 3 hours, then concentrated in vacuo and the residue dissolved in ethyl acetate (100 ml), washed with water (100 ml), dried (MgSO$_4$) and concentrated to give the product as an off-white solid (3.22 g, 90%); NMR δ(CD$_3$SOCD$_3$) 1.25 (t, 3H), 4.25 (q, 2H). 4.80 (d, 2H), 5.20 (m, 1H), 5.80 (s, 2H), 6.85 (m, 1H) 7.10 (d, 1H), 7.30 (m, 2H), 7.50 (m, 3H, M/z (+) 378.3 (MH$^+$).

Preparation 3

Ethyl 4-formyl-N-(3,4-dichlorobenzyl)indole-2-carboxylate

Ethyl N-(3,4-dichlorobenzyl)-4-hydroxymethylindole-2-carboxylate (5.17 g) and 2,3-dichloro-5,6-dicyanobenzoquinone (3.10 g) were stirred in dioxane (100 ml) at ambient temperature, overnight. The reaction mixture was concentrated in vacuo and the residue dissolved in dichloromethane (100 ml) and filtered. The filtrate was concentrated in vacuo and the residue purified by column chromatography using 10% ethyl acetate:iso-hexane as eluent to give product as a yellow solid (4.88 g, 95%); NMR δ(CD$_3$SOCD$_3$) 1.30 (t, 3H), 4.30 (q, 2H), 5.90 (s, 2H), 6.85 (m, 1H), 7.90 (m, 1H), 8.00 (m, 1H), 10.22 (s, 1H); M/z (+) 376.3 (MH$^+$).

Preparation 4

N-(3,4-Dichlorobenzyl)-2-ethoxycarbonylindole-4-carboxylic acid

A solution of sodium chlorite (9.70 g) and sodium dihydrogen orthophosphate (13.02 g) in water (50 ml) was added dropwise to a solution of ethyl 4-formyl-N-(3,4-dichlorobenzyl)indole-2-carboxylate (4.47 g) and 2-methylbut-2-ene (50 ml) in tert-butyl alcohol (100 ml) and the mixture stirred for 72 hours at ambient temperature, then concentrated in vacuo and the resulting precipitate was filtered and dried to give the product as an off-white solid (4.16 g. 89%); NMR δ(CD$_3$SOCD$_3$) 1.25 (t, 3H), 4.30 (q, 2H)) 5.85 (s, 2H), 6.85 (m, 1H), 7.35 (m, 1H), 7.40 (q, 1H), 7.50 (m, 1H), 7.80 (m, 3H); M/z (−) 390.1 (M−H$^+$).

Preparation 5

Ethyl 4-chloromethyl-N-(3,4-dichlorobenzyl)indole-2-carboxylate

Ethyl N-(3,4-dichlorobenzyl)-4-hydroxymethylindole-2-carboxylate (0.89 g), dimethylformamide (0.5 ml) and thionyl chloride (189 μl) in dichloromethane (40 ml) were stirred at ambient temperature overnight and the resulting precipitate as filtered and dried in vacuo to give the product as a white solid (0.62 g, 67%); NMR δ(CD$_3$SOCD$_3$) 1.30 (t, 3H), 4.30 (q, 2H), 5.10 (s, 2H), 5.85 (s, 2H), 6.90 (m, 1H), 7.30 (m, 3H) 7.55 (m, 3H), M/z (+) 396.2 (MH$^+$).

Preparation 6

Ethyl 5-hydroxyindole-2-carboxylate

Boron tribromide (64.58 g) was added dropwise to a stirred solution of ethyl 5-methoxyindole-2-carboxylate (20 g) in dry dichloromethane (1000 ml) at −78° C. under an atmosphere of argon. The reaction was allowed to warm to room temperature and stirred for a further 2 hours. The reaction was poured into ice/saturated aqueous sodium hydrogen carbonate solution with stirring and extracted with ethyl acetate. Combined organic extracts were washed with saturated aqueous sodium hydrogen carbonate solution, water, aqueous saturated sodium chloride solution and dried (MgSO$_4$). The solution was concentrated in vacuo and the residue was purified by column chromatography using 0–60% diethyl ether iso-hexane as eluent to give product as a white solid (9.02 g, 48%); NMR δ(CD$_3$SOCD$_3$) 1.31 (t, 3H), 4.29 (q, 2H), 6.79 (dd, 1H), 6.90 (dd, 1H), 7.22 (d, 1H), 8.84 (s, 1H), 11.52 (brs, 1H), M/z (+) 206 (MH$^+$).

Preparation 7

Ethyl 5-acetoxyindole-2-carboxylate

A stirred solution of ethyl 5-hydroxyindole-2-carboxylate (7.79 g) and DMAP (20 mg) in acetic anhydride (80 ml) was heated at 80° C. for 4 hours. The reaction was concentrated in vacuo and the residue was dissolved in ethyl acetate. Combined organic extracts were washed with hydrochloric acid (2.0 M), saturated aqueous sodium hydrogen carbonate solution, water, aqueous saturated sodium chloride solution and dried (MgSO$_4$). The solution was concentrated in vacuo to give the product as a yellow solid (9.39 g, 100%): NMR δ(CD$_3$SOCD$_3$) 1.20 (t, 3H), 2.10 (s, 3H), 4.19 (q, 2H), 6.86 (dd, 1H), 6.97 (d, 1H), 7.20 (s, 1), 7.29 (d, 1H); M/z (+) 248 (MH$^+$).

Preparation 8

Ethyl 5-acetoxy-N-(3,4-dichlorobenzyl)indole-2-carboxylate 3,4-Dichlorobenzyl bromide (5.96 g) was added to a stirred solution of ethyl 5-acetoxyindole-2-carboxylate (5.4 g) and potassium carbonate (6.94 g) in acetonitrile (500 ml) under an atmosphere of argon. The reaction was heated at 80° C. for 16 hours, then concentrated in vacuo and the residue partitioned between ethyl acetate and water. Combined organic extracts were washed with water, saturated aqueous sodium chloride and dried (MgSO$_4$). The solvent was removed in vacuo and the residue was triturated with iso-hexane to give the product as a cream solid (5.55 g, 63%): NMR δ(CD$_3$SOCD$_3$) 1.27 (t, 3H), 2.27 (s, 3H), 4.28 (q, 2H), 5.82 (s, 2H), 6.90 (d, 1H), 7.09 (dd, 1H), 7.33–7.40 (m, 2H), 7.46 (d, 1H), 7.52 (d, 1H), 7.60 (d, 1H).

Preparation 9

Ethyl N-(3,4-dichlorobenzyl)-5-hydroxyindole-2-carboxylate

Sodium ethoxide (1.86 g) was added to a stirred solution of ethyl 5-acetoxy-N-(3,4-dichlorobenzyl)indole-2-carboxylate (5.55 g) in ethanol (50 ml) under an atmosphere of argon. The reaction was stirred at room temperature for 2 hours, then concentrated in vacuo and the residue acidified with aqueous hydrochloric acid (2.0 M) and extracted with dichloromethane. Combined organic extracts were washed with water, saturated aqueous sodium chloride solution and dried (MgSO$_4$). The solvent was removed in vacuo and the residue was triturated with hexane/diethyl ether to give the product as a white solid (3.17 g, 92%); NMR δ(CD$_3$SOCD$_3$) 1.26 (t, 3H), 4.25 (q, 2H), 5.75 (s, 2H), 6.81–6.91 (m, 2H), 6.98 (d, 1H), 7.19 (s, 1H), 7.29 (d, 1H), 7.38 (d, 1H), 7.50 (d, 1H), 9.06 (s, 1H); M/z (+) 364 (MH$^+$).

EXAMPLE 1

Compound 1 Ethyl Ester

N-(3,4-Dichlorobenzyl)-2-ethoxycarbonylindole-4-carboxylic acid (100 mg), DMF (1 drop) and a solution of oxalyl chloride in dichloromethane (2M, 140 μl) were stirred in dichloromethane (4 ml) under argon, at ambient temperature, for 7 hours. The reaction mixture was concentrated in vacuo and dissolved in dichloromethane (4 ml), 3-amino-tetrahydrothiophene-1,1-dioxide (69 mg) and triethylamine (71 μl) were added and the reaction stirred under argon, overnight. The reaction mixture was diluted with dichloromethane (20 ml), washed with aq, 2M HCl (30 ml) and water (30 ml), dried (MgSO$_4$), concentrated in vacuo and the residue purified by column chromatography using ethyl acetate:iso-hexane (gradient 25/75-100/0) as eluent to give the product as an off-white solid (73 mg, 56%). M/z (+) 509.3 (MH$^+$).

EXAMPLE 2

The procedure described in Example 1 above was repeated using the appropriate amine. Thus were obtained the compounds described below.

Compound 4 Ethyl Ester

48% yield; M/z (+) 461.5 (MH$^+$).

Compound 2 Ethyl Ester

96% yield; M/z (+) 500.4 (MH$^+$).

Compound 3 Ethyl Ester

60% yield; M/z (+) 509.3 (MH$^+$).

Compound 6 Ethyl Ester

63% yield; M/z (+) 462.2 (MH$^+$).

Compound 7 Ethyl Ester

72% yield; M/z (+) 503.2 (MH$^+$).

Compound 8 Ethyl Ester

51% yield; M/z (+) 500.2 (MH$^+$).

Compound 9 Ethyl Ester

13% yield, M/z (+) 512.1 (MH$^+$).

EXAMPLE 3

Compound 10 Ethyl Methyl Diester

N-(3,4-Dichlorobenzyl)-2-ethoxycarbonylindole-4-carboxylic acid (150 mg), L-histidine methyl ester dihydrochloride (93 mg), 2-ethoxy-1-ethoxycarbonyl-1,2-dihydroquinoline (123 mg) and triethylamine (107 µl) were stirred in dichloromethane (15 ml) at ambient temperature, overnight. The reaction mixture was concentrated in vacuo and the residue purified by column chromatography using ethyl acetate:iso-hexane (gradient 10/90-100/0) then 10% methanol ethyl acetate as eluent to give product as a white gum (35 mg, 17%); M/z (+) 543.2 (MH$^+$).

EXAMPLE 4

Compound 4

Compound 4 ethyl ester (50 mg) was dissolved in tetrahydrofuran (2 ml). Aqueous sodium hydroxide (2M, 2 ml) and methanol (1 ml) were added and the mixture stirred at ambient temperature for 2 hours, then concentrated in vacuo and the residue dissolved in water (4 ml), acidified with acetic acid and resulting precipitate filtered, washed with water and dried in vacuo to give the product as a white solid (19 mg, 40%); NMR δ(CD$_3$SOCD$_3$) 3.30–3.90 (m, 8H), 6.00 (s, 2H), 7.05 (m, 1H), 7.20 (m, 2H), 7.40 (t, 1H), 7.50 (m, 1H), 7.60 (m, 1H), 7.70 (m, 1H); M/z (−) 431.4 (M−H$^-$).

EXAMPLE 5

The procedure described in Example 4 above was repeated using the appropriate ester. Thus were obtained the compounds described below.

Compound 1

77% yield; NMR δ(CD$_3$SOCD$_3$) 2.20 (m, 1H), 3.05–3.60 (m, 5H), 4.70 (m, 1H), 5.90 (s, 2H), 6.90 (m, 1H), 7.30 (m, 2H), 7.50 (m, 2H), 7.60 (s, 1H), 7.70 (m, 1H), 8.70 (d, 1H), M/z (−) 481.3 (M−H$^-$).

Compound 2

90% yield; NMR δ(CD$_3$SOCD$_3$) 2.20 (s, 3H), 2.40 (s, 3H), 4.20 (d, 2H), 6.00 (s, 2H), 7.00 (m, 1H), 7.20 (t, 1H), 7.35 (m, 3H), 7.50 (m, 1H), 7.55 (m, 1H), 8.60 (t, 1H); M/z (−) 470.1 (M−H$^-$).

Compound 3

53% yield; M/z (−) 479.1 (M−H$^-$).

Compound 6

81% yield; NMR δ(CD$_3$SOCD$_3$) 2.40 (m, 6H), 2.75 (m, 2H), 3.45 (m, 2H), 5.85 (s, 2H), 6.85 (m, 1H), 7.25 (n, 2H), 7.45 (m, 2H), 7.60 (m, 2H), 8.35 (m, 1H); M/z (−) 432.2 (M−H$^-$).

Compound 7

98% yield; NMR δ(CD$_3$SOCD$_3$) 3.22 (m, 2H), 3.40 (m, 2H), 5.90 (s, 2H), 6.23 (s, 1H), 6.90 (m, 1H), 7.30 (m, 2H), 7.50 (m, 2H), 7.65 (m, 2H), 8.40 (m, 1H); M/z (−) 473.2 (M−H$^-$).

Compound 8

100% yield; M/z (−) 470.2 (M−H$^-$).

Compound 9

85% yield; NMR δ(CD$_3$SOCD$_3$) 2.90 (s, 3H), 3.15 (m, 2H), 3.40 (m, 2H), 5.95 (s, 2), 6.90 (m, 1H), 7.15 (m, 1H), 7.30 (m, 2H), 7.50 (m, 2H), 7.60 (m, 1H), 7.65 (m, 1H), 8.40 (m, 1H); M/z (−) 482.4 (M−H$^-$).

Compound 10

51% yield; M/z (−) 499.1 (M−H$^-$).

Compound 11

50% yield; NMR δ(CD$_3$SOCD$_3$) 2.40 (m, 4H), 3.50 (m, 4H), 3.70 (s, 2H), 5.85 (s, 2H), 6.90 (m, 1H), 7.05 (m, 1H), 7.20 (m, 1H), 7.30–7.60 (m, 4H); M/z (−) 417.2 (M−H$^-$).

EXAMPLE 6

Compound 11 Ethyl Ester

Ethyl 4-chloromethyl-N-(3,4-dichlorobenzyl)indole-2-carboxylate (150 mg), morpholine (50 µl) and triethylamine (106 µl) in tetrahydrofuran (5 ml) were stirred at ambient temperature for 4 days, then concentrated in vacuo. The residue was dissolved in ethyl acetate (30 ml), washed with water (30 ml), dried (MgSO$_4$), and concentrated in vacuo. The crude residue was triturated with toluene and the resulting white solid filtered and dried (79 mg, 47%); NMR δ(CDCl$_3$) 1.42 (t, 3H), 2.98 (m, 2H), 3.37 (m, 2H), 3.95 (m, 2H), 4.20–4.60 (m, 6H), 5.80 (s, 2H), 6.90 (m, 3H), 7.20 (m, 1H), 7.25–7.60 (m, 4H), 7.70 (m, 1); M/z (+) 447.3 (MH$^+$).

EXAMPLE 7

Ethyl N-(3,4-dichlorobenzyl)-4-dimethylaminomethyl-5-hydroxyindole-2-carboxylate (Ethyl Ester of Compound 5)

To a stirred solution of ethyl N-(3,4-dichlorobenzyl)-5-hydroxyindole-2-carboxylate (2.1 g) in ethanol (50 ml) was added successively aqueous dimethylamine (40%, 0.5 ml) and aqueous formaldehyde (0.5 ml). The solution was allowed to stand overnight and the resulting crystals filtered and dried in vacuo to give the product as pale yellow crystals (1.7 g, 70%); NMR $\delta(CD_3SOCD_3)$ 1.24 (t, 3H), 2.23 (s, 6H), 3.81 (s, 2H), 4.24 (q, 2H), 5.75 (s, 2H), 6.82 (d, 1H), 6.90 (dd, 1H), 7.30 (m, 3H), 7.50 (d, 1H); M/z (+) 423.421 (MH−), 378, 376.

EXAMPLE 8

N-(3,4-dichlorobenzyl)-4-dimethylaminomethyl-5-hydroxyindole-2-carboxylic Acid (Compound 5)

Using the method of Example 5, the ester from Example 7 was converted to the title compound.

72% yield: NMR $\delta(CD_3SOCD_3)$ 2.43 (s, 6H), 4.04 (s, 2H), 5.85 (s, 2H), 6.78 (d, 1H), 7.00 (dd, 1H), 7.18 (s, 1H), 7.22 (d, 1H), 7.34 (s, 1H), 7.42 (d, 1H): M/z (+) 393, 391 (MH−), 348, 347.

EXAMPLE 9

Biological Assay's for hMCP-1 Antagonists
Biological Testing

The following biological test methods, data and Examples serve to illustrate the present invention.
Abbreviations

| | |
|---|---|
| ATCC | American Type Culture Collection, Rockville, USA. |
| BCA | Bicinchroninic acid, (used with copper sulphate, to assay protein) |
| BSA | Bovine Serum Albumin |
| DMEM | Dulbecco's modified Eagle's medium |
| EGTA | Ethylenebis(oxyethylenenitrilo)tetraacetic acid |
| FCS | Foetal calf serum |
| HEPES | (N-[2-Hydroxyethyl]piperazine-N'-[2-ethanesulphonic acid]) |
| HBSS | Hank's Balanced Salt Solution |
| hMCP-1 | Human Monocyte Chemoattractant Protein-1 |
| PBS | Phosphate buffered saline |
| PCR | Polymerase chain reaction |

AMPLITAQ™, available from Perkin-Elmer Cetus, is used as the source of thermostable DNA polymerase.

Binding Buffer is 50 mM HEPES, 1 mM $CaCl_2$, 5 mM $MgCl_2$, 0.5% foetal calf serum, adjusted to pH 7.2 with 1 M NaOH.

Non-Essential Amino Acids (100×concentrate) is: L-Alanine, 890 mg/l; L-Asparagine, 1320 mg/l; L-Aspartic acid, 1330 mg/l; L-Glutamic acid, 1470 mg/l; Glycine, 750 mg/l; L-Proline, 1150 mg/l and; L-Serine, 1050 mg/l.

Hypoxanthine and Thymidine Supplement (50× concentrate) is: hypoxanthine, 680 mg/l and; thymidine, 194 mg/l.

Penicillin-Streptomycin is: Penicillin G (sodium salt); 5000 units/ml; Streptomycin sulphate. 5000 μg/ml.

Human monocytic cell line THP-1 cells are available from ATCC, accession number ATCC TIB-202.

Hank's Balanced Salt Solution (HBSS) was obtained from Gibco; see Proc. Soc. Exp. Biol. Med., 1949, 71, 196.

Synthetic cell culture medium, RPMI 1640 was obtained from Gibco; it contains inorganic salts [$Ca(NO_3)_2.4H_2O$ 100 mg/l; KCl 400 mg/l; $MgSO_4.7H_2O$ 100 mg/l; NaCl 6000 mg/l; $NaHCO_3$ 2000 mg/l & $Na_2HPO_4$ (anhyd) 800 mg/l], D-Glucose 2000 mg/l, reduced glutathione 1 mg/l, amino acids and vitamins.

FURA-2/AM is 1-[2-(5-carboxyoxazol-2-yl)-6-aminobenzofuran-5-oxy]-2-(2'-amino-5'-methylphenoxy)-ethane-N,N,N',N'-tetraacetic acid pentaacetoxymethyl ester and was obtained from Molecular Probes, Eugene, Oreg., USA.

Blood Sedimentation Buffer contains 8.5 g/l NaCl and 10 g/l hydroxyethyl cellulose.

Lysis Buffer is 0.15M $NH_4Cl^−$, 10 mM $KHCO_3$, 1 mM EDTA

Whole Cell Binding Buffer is 50 mM HEPES, 1 mM $CaCl_2$, 5 mM $MgCl_2$, 0.5% BSA, 0.01% $NaN_3$, adjusted to pH 7.2 with 1M NaOH.

Wash buffer is 50 mM HEPES, 1 mM $CaCl_2$, 5mM $MgCl_2$, 0.5% heat inactivated FCS, 0.5MNaCl adjusted to pH7.2 with 1M NaOH.

General molecular biology procedures can be followed from any of the methods described in "Molecular Cloning—A Laboratory Manual" Second Edition, Sambrook, Fritsch and Maniatis (Cold Spring Harbor Laboratory, 1989).

i) Cloning and Expression of hMCP-1 Receptor

The MCP-1 receptor B (CCR2B) cDNA was cloned by PCR from THP-1 cell RNA using suitable oligonucleotide primers based on the published MCP-1 receptor sequences (Charo et al., 1994, *Proc. Natl. Acad. Sci. USA*, 91, 2752). The resulting PCR products were cloned into vector PCR-II™ (InVitrogen, San Diego, Calif.). Error free CCR2B cDNA was subcloned as a Hind III-Not I fragment into the eukaryotic expression vector pCDNA3 (InVitrogen) to generate pCDNA3/CC-CKR2A and pCDNA3/CCR2B respectively.

Linearised pCDNA3/CCR2B DNA was transfected into CHO-K1 cells by calcium phosphate precipitation (Wigler et al., 1979, *Cell*, 16, 777). Transfected cells were selected by the addition of Geneticin Sulphate (G418, Gibco BRL) at 1 mg/ml, 24 hours after the cells had been transfected. Preparation of RNA and Northern blotting were carried out as described previously (Needham et al., 1995, *Prot. Express. Purific.*, 6. 134). CHO-K1 clone 7 (CHO-CCR2B) was identified as the highest MCP-1 receptor B expressor.

ii) Preparation of Membrane Fragments

CHO-CCR2B cells were grown in DMEM supplemented with 10% foetal calf serum, 2 mM glutamine. 1×Non-Essential Amino Acids. 1×Hypoxanthine and Thymidine Supplement and Penicillin-Streptomycin (at 50 μg streptomycin/ml, Gibco BRL). Membrane fragments were prepared using cell lysis/differential centrifugation methods as described previously (Siciliano et al., 1990, *J. Biol. Chem.*, 265, 19658). Protein concentration was estimated by BCA protein assay (Pierce, Rockford, Ill.) according to the manufacturer's instructions.

iii) Assay $^{125}I$ MCP-1 was prepared using Bolton and Hunter conjugation (Bolton et al., 1973, *Biochem. J.*, 133, 599; Amersham International plc]. Equilibrium binding assays were carried out using the method of Ernst et al., 1994, *J. Immunol.*, 152, 3541. Briefly, varying amounts of $^{125}I$-labeled MCP-1 were added to 7 μg of purified CHO-CCR2B cell membranes in 100 μl of Binding Buffer. After 1 hour incubation at room temperature the binding reaction mixtures were filtered and washed 5 times through a plate washer (Brandel MLR-96T Cell Harvester) using ice cold Binding Buffer. Filter mats (Brandel GF/B) were pre-soaked for 60 minutes in 0.3% polyethylenimine prior to use. Following filtration individual filters were separated into 3.5 ml tubes (Sarstedt No. 55.484) and bound $^{125}I$-labeled MCP-I was determined (LKB 1277 Gammamaster). Cold competition studies were performed as above using 100 pM $^{125}I$-labeled MCP-1 in the presence of varying concentrations of unlabelled MCP-1. Non-specific binding was determined by the inclusion of a 200-fold molar excess of unlabelled MCP-1 in the reaction.

Ligand binding studies with membrane fragments prepared from CHO-CCR2B cells showed that the CCR2B receptor was present at a concentration of 0.2 pmoles/mg of membrane protein and bound MCP-1 selectively and with high affinity ($IC_{50}$=110 pM, $K_d$=120 pM). Binding to these membranes was completely reversible and reached equilibrium after 45 minutes at room temperature, and there was a linear relationship between MCP-1 binding and CHO-CCR2B cell membrane concentration when using MCP-1 at concentrations between 100 pm and 500 pM.

Test compounds dissolved in DMSO (5 μl) were tested in competition with 100 pM labelled MCP-1 over a concentration range (0.01–50 μM) in duplicate using eight point dose-response curves and $IC_{50}$ concentrations were calculated.

Compounds tested of the present invention had $IC_{50}$ values of 50 μM or less in the hMCP-1 receptor binding assay described herein.

b) MCP-1 Mediated Calcium Flux in THP-1 Cells

The human monocytic cell line THP-1 as grown in a synthetic cell culture medium RPMI 1640 supplemented with 10% foetal calf serum, 6 mM glutamine and Penicillin-Streptomycin (at 50 μg streptomycin/ml, Gibco BRL). THP-1 cells were washed in HBSS (lacking $Ca^{2+}$ and $Mg^{2+}$)+1 mg/ml BSA and resuspended in the same buffer at a density of $3\times10^6$ cells/ml. The cells were then loaded with 1 mM FURA-2/AM for 30 min at 37° C., washed twice in HBSS, and resuspended at $1\times10^6$ cells/ml. THP-1 cell suspension (0.9 ml) was added to a 5 ml disposable cuvette containing a magnetic stirrer bar and 2.1 ml of prewarmed (37° C.) HBSS containing 1 mg/ml BSA, 1 mM MgCl, and 2 mM $CaCl_2$. The cuvette was placed in a fluorescence spectrophotometer (Perkin Elmer, Norwalk. Conn.) and pre-incubated for 4 min at 37° C. with stirring. Fluorescence was recorded over 70 sec and cells were stimulated by addition of hMCP-1 to the cuvette after 10 sec. $[Ca^{2+}]i$ was measured by excitation at 340 nm and 380 nm alternately and subsequent measurement of the intensity of the fluorescence emission at 510 nm. The ratio of the intensities of the emitted fluorescent light following excitation at 340 nm and 380 nm, (R), was calculated and displayed to give and estimate of cytoplasmic $[Ca^{2+}]$ according to the equation:

$$[Ca^{2+}]i = \frac{K_d(R - Rmin)(Sf2/Sb2)}{(Rmax - R)}$$

where the $K_d$ for FURA-2 $Ca^{2+}$ complex at 37° C. was taken to be 224 nm. $R_{max}$ is the maximal fluorescence ratio determined after addition of 10 mM Ionomycin, $R_{min}$ is the minimal ratio determined by the subsequent addition of a $Ca^{2+}$ free solution containing 5 mM EGTA, and Sf2/Sb2 is the ratio of fluorescence values at 380 nm excitation determined at $R_{min}$ and $R_{max}$, respectively.

Stimulation of THP-1 cells with hMCP-1 induced a rapid, transient rise in $[Ca^{2+}]_i$ in a specific and dose dependent manner. Dose response curves indicated an approximate $EC_{50}$ of 2 nm. Test compounds dissolved in DMSO (10 μl) were assayed for inhibition of calcium release by adding them to the cell suspension 10 sec prior to ligand addition and measuring the reduction in the transient rise in $[Ca^{2+}]i$. Test compounds were also checked for lack of agonist activity by addition in place of hMCP-1.

c) hMCP-1 and RANTES Mediated Chemotaxis

In vitro chemotaxis assays were performed using the human monocytic cell line THP-1. Cell migration through polycarbonate membranes was measured by enumerating those passing through either directly by Coulter counting or indirectly by use of a colourimetric viability assay measuring the cleavage of a tetrazolium salt by the mitochondrial respiratory chain (Scudiero D. A. et al. 1988, *Cancer Res.*, 48, 4827–4833).

Chemoattractants were introduced into a 96-well microtitre plate which forms the lower well of a chemotaxis chamber fitted with a PVP-free 5 μm poresize polycarbonate adhesive framed filter membrane (NeuroProbe MB series, Cabin John, Md. 20818. USA) according to the manufacturer's instructions. The chemoattractant was diluted as appropriate in synthetic cell culture medium, RPMI 1640 (Gibco) or supplemented with 2 mM glutamine and 0.5% BSA. or alternatively with HBSS with $Ca^{2-}$ and $Mg^{2+}$ without Phenol Red (Gibco) plus 0.1% BSA. Each dilution was degassed under vacuum for 30 min and was placed (400 μl) in the lower wells of the chamber and THP-1 cells ($5\times10^5$ in 100 μl RPMI 1640+0.5%BSA) were incubated in each well of the upper chamber. For the inhibition of chemotaxis the chemoattractant was kept at a constant submaximal concentration determined previously (1 nM MCP-1) and added to the lower well together with the test compounds dissolved in DMSO (final DMSO concentration<0.05% v/v) at varying concentrations. The chamber was incubated for 2 h at 37° C. under 5% $CO_2$. The medium was removed from the upper wells which were then washed out with 200 μl physiological saline before opening the chamber, wiping dry the membrane surface and centrifuging the 96-well plate at 600 g for 5 min to harvest the cells. Supernatant (150 μl) was aspirated and 10 μl of cell proliferation reagent, WST-1, {4-[3-(4-iodophenyl)-2-(4-nitrophenyl)-2H-5-tetrazolio]-3-phenyl disulfonate} plus an electron coupling reagent (Boehringer Mannheim, Cat.no. 1644 807) was added back to the wells. The plate was incubated at 37° C. for 3 h and the absorbance of the soluble formazan product was read on a microtitre plate reader at 450 nm. The data was input into a spreadsheet, corrected for any random migration in the absence of chemoattractant and the average absorbance values, standard error of the mean, and significance tests were calculated. hMCP-1 induced concentration dependent cell migration with a characteristic biphasic response, maximal 0.5–1.0 nm.

In an alternative form of the above assay, fluorescently tagged cells can be used in order to assist in end point detection. In this case, the THP-1 cells used are fluorescently tagged by incubation in the presence of 5 mM Calcein AM (Glvcine, N,N'-[[3',6'-bis(acetyloxy)-3-oxospiro [isobenzofuran-1(3H),9'-[9H]xanthene]-2',7'-diyl]bis (methylene)]bis[N-[2-[(acetyloxy)methoxy]-2-oxoethyl]]-bis[(acetyloxy)methyl] ester; Molecular Probes) for 45 minutes in the dark. Cells are harvested by centrifugation and resuspended in HBSS (without Phenol Red) with $Ca^{2-}$ $Mg^{2-}$ and 0.1% BSA. 50 μl ($2\times105$ cells) of the cell suspension are placed on the filter above each well and, as above, the unit is incubated at 37° C. for 2 hours under 5% $CO_2$. At the end of the incubation, cells are washed off the upper face of the filter with phosphate buffered saline, the filter removed from the plate and the number of cells attracted to either the underside of the filter or the lower well estimated by reading fluorescence at 485 nm excitation, 538 nm emission wavelengths (fmax, Molecular Devices). The data was input into a spreadsheet, corrected for any random migration in the absence of chemoattractant and the average fluorescence values, standard error of the mean, percentage inhibition and $IC_{50}$ of compounds under test and significance tests can be calculated. In addition to MCP-1 induced chemotaxis, this alternative form of the assay was also used to measure inhibition of RANTES (2 nM) induced chemotaxis.

d) Binding to Human Peripheral Blood Mononuclear Cells (PBMCs)

i) Preparation of Human PBMCs

Fresh human blood (200 ml) was obtained from volunteer donors, collected into sodium citrate anticoagulant to give a final concentration of 0.38%. The blood was mixed with Sedimentation Buffer and incubated at 37° C. for 20 minutes. The supernatant was collected and centrifuged at 1700 rpm for 5 minutes (Sorvall RT6000D). The pellet obtained was resuspended in 20 ml RPMI/BSA (1 mg/ml) and 4×5 mls of cells were carefully layered over 4×5 mls of Lymphoprepa (Nycomed) in 15 ml centrifuge tubes. Tubes were spun at 1700 rpm for 30 minutes (Sorvall RT6000D) and the resultant layer of cells was removed and transferred to 50 ml Falcon tubes. The cells were washed twice in Lysis Buffer to remove any remaining red blood cells followed by 2 washes in RPMI/BSA. Cells were resuspended in 5 mls of Binding Buffer. Cell number was measured on a Coulter counter and additional binding buffer was added to give a final concentration of $1.25 \times 10^7$ PBMCs/ml.

ii) Assay

[$^{125}$I]MCP-1 was prepared using Bolton and Hunter conjugation (Bolton et al., 1973, *Biochem. J.*, 133, 529; Amersham International plc]. Equilibrium binding assays were carried out using the method of Ernst et al., 1994, *J. Immunol.*, 152, 3541. Briefly, 50 µl of $^{125}$I-labeled MCP-1 (final concentration 100 pM) was added to 40 µl ($5 \times 10^5$ cells) of cell suspension in a 96 well plate. Compounds. diluted in Whole Cell Binding Buffer from a stock solution of 10 mM in DMSO were added in a final volume of 5 µl to maintain a constant DMSO concentration in the assay of 5%. Total binding was determined in the absence of compound. Non-specific binding was defined by the addition of 5 µl cold MCP-1 to give a final assay concentration of 100 nM. Assay wells were made up to a final volume of 100 µl with Whole Cell Binding Buffer and the plates sealed. Following incubation at 37° C. for 60 minutes the binding reaction mixtures were filtered and washed for 10 seconds using ice cold Wash Buffer using a plate washer (Brandel MLR-96T Cell Harvester). Filter mats (Brandel GF/B) were pre-soaked for 60 minutes in 0.3% polyethylenimine plus 0.2% BSA prior to use. Following filtration individual filters were separated into 3.5 ml tubes (Sarstedt No. 55.484) and bound $^{125}$I-labeled MCP-1 was determined (LKB 177 Gammamaster).

Test compound potency was determined by assay in duplicate using six point dose-response curves and $IC_{50}$ concentrations were determined.

Compounds tested of the present invention had $IC_{50}$ values of less than 5 µM in the hMCP-1 receptor binding assay described herein. For example compound 9 had an $IC_{50}$ of 0.64 µM.

No physiologically unacceptable toxicity was observed at the effective dose for compounds tested of the present invention.

EXAMPLE 10

Pharmaceutical Compositions

The following Example illustrates, but is not intended to limit, pharmaceutical dosage forms of the invention as defined herein (the active ingredient being termed "Compound X"), for therapeutic or prophylactic use in humans:

(a)

| Tablet I | mg/tablet |
|---|---|
| Compound X | 100 |
| Lactose Ph.Eur | 182.75 |
| Croscarmellose sodium | 12.0 |
| Maize starch paste (5% w/v paste) | 2.25 |
| Magnesium stearate | 3.0 |

(b)

| Tablet II | mg/tablet |
|---|---|
| Compound X | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

(c)

| Tablet III | mg/tablet |
|---|---|
| Compound X | 1.0 |
| Lactose Ph.Eur | 93.25 |
| Croscarmellose sodium | 4.0 |
| Maize starch paste (5% w/v paste) | 0.75 |
| Magnesium stearate | 1.0 |

(d)

| Capsule | mg/capsule |
|---|---|
| Compound X | 10 |
| Lactose Ph.Eur | 488.5 |
| Magnesium | 1.5 |

(e)

| Injection I | (50 mg/ml) |
|---|---|
| Compound X | 5.0% w/v |
| 1M Sodium hydroxide solution | 15.0% v/v |
| 0.1M Hydrochloric acid | to adjust pH to 7.6 |
| Polyethylene glycol 400 | 4.5% w/v |
| Water for injection | to 100% |

(f)

| Injection II | (10 mg/ml) |
|---|---|
| Compound X | 1.0% w/v |
| Sodium phosphate BP | 3.6% w/v |
| 0.1M Sodium hydroxide solution | 15.0% v/v |
| Water for injection | to 100% |

(g)

| Injection III | (1 mg/ml. buffered to pH6) |
|---|---|
| Compound X | 0.1% w/v |
| Sodium phosphate BP | 2.26% w/v |
| Citric acid | 0.38% w/v |
| Polyethylene glycol 400 | 3.5% w/v |
| Water for injection | to 100% |

(h)

| Aerosol I | mg/ml |
|---|---|
| Compound X | 10.0 |
| Sorbitan trioleate | 13.5 |
| Trichlorofluoromethane | 910.0 |
| Dichlorodifluoromethane | 490.0 |

-continued

(i)

| Aerosol II | mg/ml |
|---|---|
| Compound X | 0.2 |
| Sorbitan trioleate | 0.27 |
| Trichlorofluoromethane | 70.0 |
| Dichlorodifluoromethane | 280.0 |
| Dichlorotetrafluoroethane | 1094.0 |

(j)

| Aerosol III | mg/ml |
|---|---|
| Compound X | 2.5 |
| Sorbitan trioleate | 3.38 |
| Trichlorofluoromethane | 67.5 |
| Dichlorodifluoromethane | 1086.0 |
| Dichlorotetrafluoroethane | 191.6 |

(k)

| Aerosol IV | mg/ml |
|---|---|
| Compound X | 2.5 |
| Soya lecithin | 2.7 |
| Trichlorofluoromethane | 67.5 |
| Dichlorodifluoromethane | 1086.0 |
| Dichlorotetrafluoroethane | 191.6 |

(l)

| Ointment | ml |
|---|---|
| Compound X | 40 mg |
| Ethanol | 300 μl |
| Water | 300 μl |
| 1-Dodecylazacycloheptan-2-one | 50 μl |
| Propylene glycol | to 1 ml |

Note:
Compound X in the above formulation may comprise a compound illustrated in Examples 1 to 6 herein. The above formulations may be obtained by conventional procedures well known in the pharmaceutical art. The tablets (a)–(c) may be enteric coated by conventional means, for example to provide a coating of cellulose acetate phthalate. The aerosol formulations (h)–(k) may be used in conjunction with standard, metered dose aerosol dispensers, and the suspending agents sorbitan trioleate and soya lecithin may be replaced by an alternative suspending agent such as sorbitan monooleate, sorbitan sesquioleate, polysorbate 80, polyglycerol oleate or oleic acid.

What is claimed is:

1. A compound of formula (I)

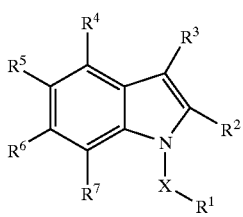

(I)

wherein

X is $CH_2$ or $SO_2$;

$R^1$ is an optionally substituted aryl or heteroaryl ring;

$R^2$ is carboxy, cyano, —$C(O)CH_2OH$, —$CONHR^8$, —$SO_2NHR^9$, tetrazol-5-yl, $SO_3H$, or a group of formula (VI)

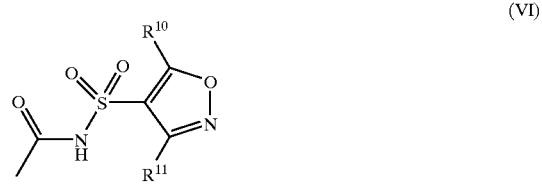

(VI)

where $R^8$ is selected from hydrogen, alkyl, aryl, cyano, hydroxy, —$SO_2R^{12}$ where $R^{12}$ is alkyl, aryl, heteroaryl, or haloalkyl, or $R^8$ is a group-$(CHR^{13})_r$—COOH where r is an integer of 1–3 and each $R^{13}$ group is independently selected from hydrogen or alkyl; $R^9$ is hydrogen, alkyl, optionally substituted aryl or optionally substituted heteroaryl, or a group $COR^{14}$ where $R^{14}$ is alkyl, aryl, heteroaryl or haloalkyl; $R^{10}$ and $R^{11}$ are independently selected from hydrogen or alkyl;

$R^3$ is hydrogen, a functional group, optionally substituted alkyl, optionally substituted alkenyl, optionally substituted alkynyl, optionally substituted aryl, optionally substituted heterocyclyl, optionally substituted alkoxy, optionally substituted aralkyl, optionally substituted aralkyloxy, or optionally substituted cycloalkyl;

$R^4$ is a group $C(O)NR^{15}R^{16}$ or a group $(CH_2)_tR^{17}$; where $R^{15}$ and $R^{16}$ are independently selected from hydrogen, optionally substituted alkyl, optionally substituted alkenyl, optionally substituted alkynyl, optionally substituted cycloalkyl or optionally substituted heterocyclyl provided that $R^{15}$ and $R^{16}$ are not both hydrogen, or $R^{15}$ and $R^{16}$ together with the nitrogen atom to which they are attached form an optionally substituted heterocyclic ring which optionally contains further heteroatoms; $R^{17}$ is selected from $NR^{18}R^{19}$, $OR^{20}$ or $S(O)_sR^{21}$, where $R^{18}$ and $R^{19}$ are independently selected from hydrogen, optionally substituted hydrocarbyl or optionally substituted heterocyclyl, or $R^{18}$ and $R^{19}$ together with the nitrogen atom to which they are attached form an optionally substituted heterocyclic ring which optionally contains further heteroatoms, $R^{20}$ is substituted alkyl, optionally substituted alkenyl, optionally substituted alkynyl, optionally substituted cycloalkyl or optionally substituted heterocyclyl, $R^{21}$ is optionally substituted hydrocarbyl or optionally substituted heterocyclyl, s is 0, 1 or 2 and t is an integer of from 1–4;

$R^5$, $R^6$ and $R^7$ are independently selected from hydrogen, a functional group, or an optionally substituted hydrocarbyl group or optionally substituted heterocyclyl group, or a pharmaceutically acceptable salt, in vivo hydrolysable ester, or amide of the compound of formula (I), wherein each occurrence of a functional group is a substituent selected from halo, cyano, nitro, $C(O)_n$ $R^{22}$, $OR^{22}$, $S(O)_mR^{22}$, $NR^{23}R^{24}$, $C(O)NR^{23}R^{24}$, $OC(O)$ $NR^{23}R^{24}$, —$NR^{23}C(O)_nR^{22}$, —$NR^{22}CONR^{23}R^{24}$, —$N=CR^{22}R^{23}$, $S(O)_mNR^{23}R^{24}$ and —$NR^{23}S(O)_m$ $R^{22}$, where $R^{22}$, $R^{23}$ and $R^{24}$ are independently selected from hydrogen or optionally substituted hydrocarbyl, or $R^{23}$ and $R^{24}$ together form an optionally substituted heterocyclic ring, which optionally contains further heteroatoms, n is an integer of 1 or 2, m is an integer of 1–2, and where optional substituents for hydrocarbyl or groups $R^{22}$, $R^{23}$ and $R^{24}$ are selected from halo, perhaloalkyl, mercapto, hydroxy, carboxy, alkoxy, heteroaryl, heteroaryloxy, alkenyloxy, alkynyloxy, alkoxyalkoxy, aryloxy (where the aryl group is optionally substituted by halo, nitro, or hydroxy), cyano, nitro, amino, mono- or di-alkyl amino, oximino and $S(O)_{m'}R^{25}$ where m' is 1 or 2, and $R^{25}$ is alkyl.

2. A compound according to claim 1 where $R^4$ is a group $C(O)NR^{15}R^{16}$ where one of $R^{15}$ or $R^{16}$ is hydrogen or alkyl and the other is optionally substituted heterocyclyl or optionally substituted alkyl, or $R^{15}$ and $R^{16}$ together with the nitrogen atom to which they are attached form an optionally substituted heterocyclic ring which optionally contains further heteroatoms.

3. A compound according to claim 2 wherein $R^4$ is a group $C(O)NR^{15}R^{16}$ where one of $R^{15}$ or $R^{16}$ is hydrogen and the other is heterocyclyl or alkyl substituted with one or more groups selected from amino, mono- or di-alkyl amino, carboxy or optionally substituted heterocyclyl.

4. A compound according to claim 2 wherein $R^4$ is a group $C(O)NR^{15}R^{16}$ and $R^{15}$ and $R^{16}$ together with the nitrogen atom to which they are attached form a morpholine ring, or $R^4$ is a group of sub-formula (IV)

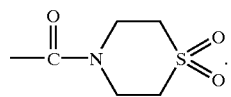

5. A compound according to claim 1 wherein $R^4$ is a group $(CH_2)_t R^{17}$ where t is 1 and $R^{17}$ is a group $NR^{18}R^{19}$ and $R^{18}$ and $R^{19}$ are as defined in claim 1.

6. A compound according to any one of the preceding claims wherein $R^1$ is 3,4-dichlorophenyl, 3-fluoro-4-chlorophenyl, 3-chloro-4-fluorophenyl or 2,3-dichloropyrid-5-yl.

7. A compound according to any one of claims 1 to 5 wherein X is $CH_2$.

8. A pharmaceutical composition comprising a compound according to any one of claims 1 to 5 in combination with a pharmaceutically acceptable carrier.

* * * * *

UNITED STATES PATENT AND TRADEMARK OFFICE
CERTIFICATE OF CORRECTION

PATENT NO. : 6,613,760 B1
DATED : September 2, 2003
INVENTOR(S) : Kettle et al.

It is certified that error appears in the above-identified patent and that said Letters Patent is hereby corrected as shown below:

Column 29,
Line 4, change "$S(O)_m R^{25}$" to -- $S(O)_{m'} R^{25}$ --.

Signed and Sealed this

Thirteenth Day of January, 2004

JON W. DUDAS
*Acting Director of the United States Patent and Trademark Office*